US012735401B2

(12) United States Patent
Muthusamy et al.

(10) Patent No.: US 12,735,401 B2
(45) Date of Patent: Sep. 15, 2026

(54) SOLID STATE FORMS OF DANICOPAN AND PROCESS THEREOF

(71) Applicant: ASSIA CHEMICAL INDUSTRIES LTD., Tel Aviv (IL)

(72) Inventors: Anantha Rajmohan Muthusamy, Sivakasi (IN); Meenakshi Sundaram Somasundaram, Virudu Nagar DT (IN)

(73) Assignee: ASSIA CHEMICAL INDUSTRIES LTD, Tel Aviv (IL)

( * ) Notice: Subject to any disclaimer, the term of this patent is extended or adjusted under 35 U.S.C. 154(b) by 238 days.

(21) Appl. No.: 18/726,464

(22) PCT Filed: Feb. 17, 2023

(86) PCT No.: PCT/US2023/013270

§ 371 (c)(1),
(2) Date: Jul. 3, 2024

(87) PCT Pub. No.: WO2023/158772

PCT Pub. Date: Aug. 24, 2023

(65) Prior Publication Data

US 2025/0066327 A1 Feb. 27, 2025

(30) Foreign Application Priority Data

Feb. 21, 2022 (IN) ............................. 202211009155
Mar. 30, 2022 (IN) ............................. 202211019074

(51) Int. Cl.
*C07D 401/14* (2006.01)
*A61K 31/506* (2006.01)
*C07D 403/14* (2006.01)
*C07K 1/30* (2006.01)
*C07K 16/18* (2006.01)

(52) U.S. Cl.
CPC .......... *C07D 401/14* (2013.01); *A61K 31/506* (2013.01); *C07D 403/14* (2013.01); *C07K 1/306* (2013.01); *C07K 16/18* (2013.01)

(58) Field of Classification Search
None
See application file for complete search history.

(56) References Cited

U.S. PATENT DOCUMENTS 9,796,741 B2 10/2017 Gadhachanda et al.
10,253,053 B2 4/2019 Wiles et al.

FOREIGN PATENT DOCUMENTS

CN 113801189 A 12/2021
WO 2020051538 A1 3/2020

OTHER PUBLICATIONS

International Search Report and Written Opinion of the International Searching Authority issued in corresponding application PCT/US2023/013270 mailed May 23, 2023 (8 pages).

*Primary Examiner* — Juliet C Switzer
*Assistant Examiner* — Dawanna Shar-Day White
(74) *Attorney, Agent, or Firm* — Carter, DeLuca & Farrell LLP

(57) ABSTRACT

The present disclosure relates to Danicopan solid state forms, processes for preparation thereof, pharmaceutical compositions thereof, and methods of use thereof.

15 Claims, 8 Drawing Sheets

XRPD Pattern of Crystalline Danicopan Pure Form DT2

XRPD Pattern of Crystalline Danicopan Form DT3

XRPD Pattern of Crystalline Danicopan Form DT4

SOLID STATE FORMS OF DANICOPAN AND PROCESS THEREOF

CROSS REFERENCE TO RELATED APPLICATIONS

This application is a National Stage of, and claims priority to and the benefit of, International Patent Application No. PCT/US2023/013270, filed on Feb. 17, 2023, which, in turn, claims the benefit of and priority to, Indian Provisional Application No. 20/221,1009155, filed on Feb. 21, 2022, and Indian Provisional Application No. 20/221,1019074, filed on Mar. 30, 2022, the entire disclosures of each of which are incorporated by reference herein.

FIELD OF THE INVENTION

The present disclosure relates to Danicopan solid state forms, processes for preparation thereof, pharmaceutical compositions thereof, and methods of use thereof.

BACKGROUND

Danicopan (ACH-4471) which has the chemical name (2S,4R)-1-(2-(3-Acetyl-5-(2-methylpyrimidin-5-yl)-1H-indazol-1-yl) acetyl)-N-(6-bromopyridin-2-yl)-4-fluoropyrrolidine-2-carboxamide is a first-in-class oral proximal, complement alternative pathway factor D (FD) inhibitor for patients with paroxysmal nocturnal hemoglobinuria (PNH) and other complement mediated diseases, optionally as an add-on therapy to a component 5 inhibitor such as ravulizumab or eculizumab. Danicopan is also being investigated for the treatment of geographic atrophy in age-related macular degeneration. As described in U.S. Pat. No. 9,796,741 Danicopan has the following chemical structure:

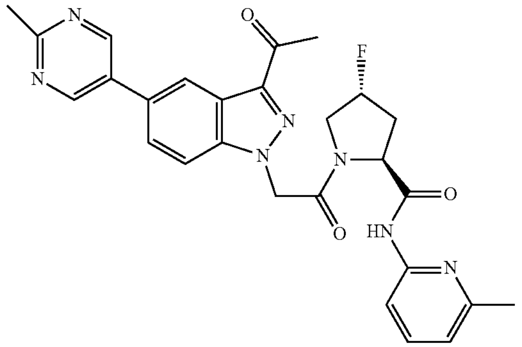

Danicopan preparation is disclosed in U.S. Pat. No. 10,253,053. Danicopan polymorphs are described in International patent application WO 2020/051538 and CN 113801189.

Polymorphism, the occurrence of different crystal forms, is a property of some molecules and molecular complexes. A single compound, like Danicopan, may give rise to a variety of polymorphs having distinct crystal structures and physical properties like melting point, thermal behaviors (e.g. measured by thermogravimetric analysis—"TGA", or differential scanning calorimetry—"DSC"), X-ray powder diffraction (XRPD) pattern, infrared absorption fingerprint, Raman absorption fingerprint, and solid state ($^{13}C$—) NMR spectrum. One or more of these techniques may be used to distinguish different polymorphic forms of a compound.

Different salts and solid state forms (including solvated forms) of an active pharmaceutical ingredient may possess different properties. Such variations in the properties of different salts and solid state forms may provide a basis for improving formulation, for example, by facilitating better processing or handling characteristics, improving the dissolution profile, or improving stability (polymorph as well as chemical stability) and shelf-life. These variations in the properties of different salts and solid state forms may also provide improvements to the final dosage form, for instance, if they serve to improve bioavailability. Different salts and solid state forms of an active pharmaceutical ingredient may also give rise to a variety of polymorphs or crystalline forms, which may in turn provide additional opportunities to use variations in the properties and characteristics of a solid active pharmaceutical ingredient for providing an improved product.

Discovering new salts and solid state forms of a pharmaceutical product can provide materials having desirable processing properties, such as ease of handling, ease of processing, storage stability, and ease of purification or as desirable intermediate crystal forms that facilitate conversion to other salts or polymorphic forms. New polymorphic forms and new salts of a pharmaceutically useful compound can also provide an opportunity to improve the performance characteristics of a pharmaceutical product (dissolution profile, bioavailability, etc.). It enlarges the repertoire of materials that a formulation scientist has available for formulation optimization, for example by providing a product with different properties, e.g., a different crystal habit, higher crystallinity or polymorphic stability which may offer better processing or handling characteristics, improved dissolution profile, or improved shelf-life. For at least these reasons, there is a need for additional salts and solid state forms (including solvated forms) of Danicopan.

SUMMARY OF THE INVENTION

The present disclosure relates to Danicopan solid state forms or crystalline polymorphs thereof, to processes for preparation thereof, and to pharmaceutical compositions comprising solid state form thereof.

In particular, the present disclosure provides crystalline forms of Danicopan designated as Forms DT1-DT6 (defined herein).

The present disclosure further provides process for preparing Danicopan and solid state forms or crystalline polymorphs thereof.

In another aspect, the present disclosure encompasses the above described solid state forms or crystalline polymorphs of Danicopan for use in the preparation of pharmaceutical compositions and/or formulations, preferably for use in medicine, preferably for treating complement mediated diseases, preferably for the treatment of patients with paroxysmal nocturnal hemoglobinuria (PNH) optionally as an add-on therapy to a component 5 inhibitor, particularly wherein the component 5 inhibitor is ravulizumab or eculizumab, or for the treatment of geographic atrophy in age-related macular degeneration.

In another aspect, the present disclosure encompasses the use of any one of the above described solid state forms or crystalline polymorphs of Danicopan for the preparation of pharmaceutical compositions and/or formulations, preferably for use in medicine, preferably for treating complement mediated diseases, preferably for the treatment of patients with paroxysmal nocturnal hemoglobinuria (PNH), optionally as an add-on therapy to a component 5 inhibitor, particularly wherein the component 5 inhibitor is ravulizumab or eculizumab, or for the treatment of geographic atrophy in age-related macular degeneration. . . . In yet another embodiment, the present disclosure encompasses pharmaceutical compositions comprising any one of the solid state forms or crystalline polymorphs of Danicopan.

In a specific embodiment, the present disclosure encompasses pharmaceutical formulations comprising the solid state forms or crystalline polymorphs of Danicopan, and at least one pharmaceutically acceptable excipient.

The present disclosure further encompasses processes to prepare said pharmaceutical formulations of Danicopan, comprising combining any one of the above described solid state forms or crystalline polymorphs of Danicopan, or pharmaceutical compositions comprising it, and at least one pharmaceutically acceptable excipient.

The solid state forms or crystalline polymorphs of Danicopan as defined herein as well as the pharmaceutical compositions or formulations comprising it can be used as medicaments, particularly for treating complement mediated diseases, preferably for the treatment of patients with paroxysmal nocturnal hemoglobinuria (PNH), optionally as an add-on therapy to a component 5 inhibitor, particularly wherein the component 5 inhibitor is ravulizumab or eculizumab, or for the treatment of geographic atrophy in age-related macular degeneration, comprising administering a therapeutically effective amount of the solid state form of the present disclosure, or at least one of the above pharmaceutical compositions or formulations, to a subject suffering from complement mediated disease, or otherwise in need of the treatment.

The present disclosure also provides the uses of the solid state forms or crystalline polymorphs of Danicopan of the present disclosure, or at least one of the above pharmaceutical compositions or formulations, for the manufacture of medicaments for treating complement mediated diseases, preferably for the treatment of patients with paroxysmal nocturnal hemoglobinuria (PNH), optionally as an add-on therapy to a component 5 inhibitor, particularly wherein the component 5 inhibitor is ravulizumab or eculizumab, or for the treatment of geographic atrophy in age-related macular degeneration.

DETAILED DESCRIPTION OF ILLUSTRATIVE EMBODIMENTS

Figure 1:
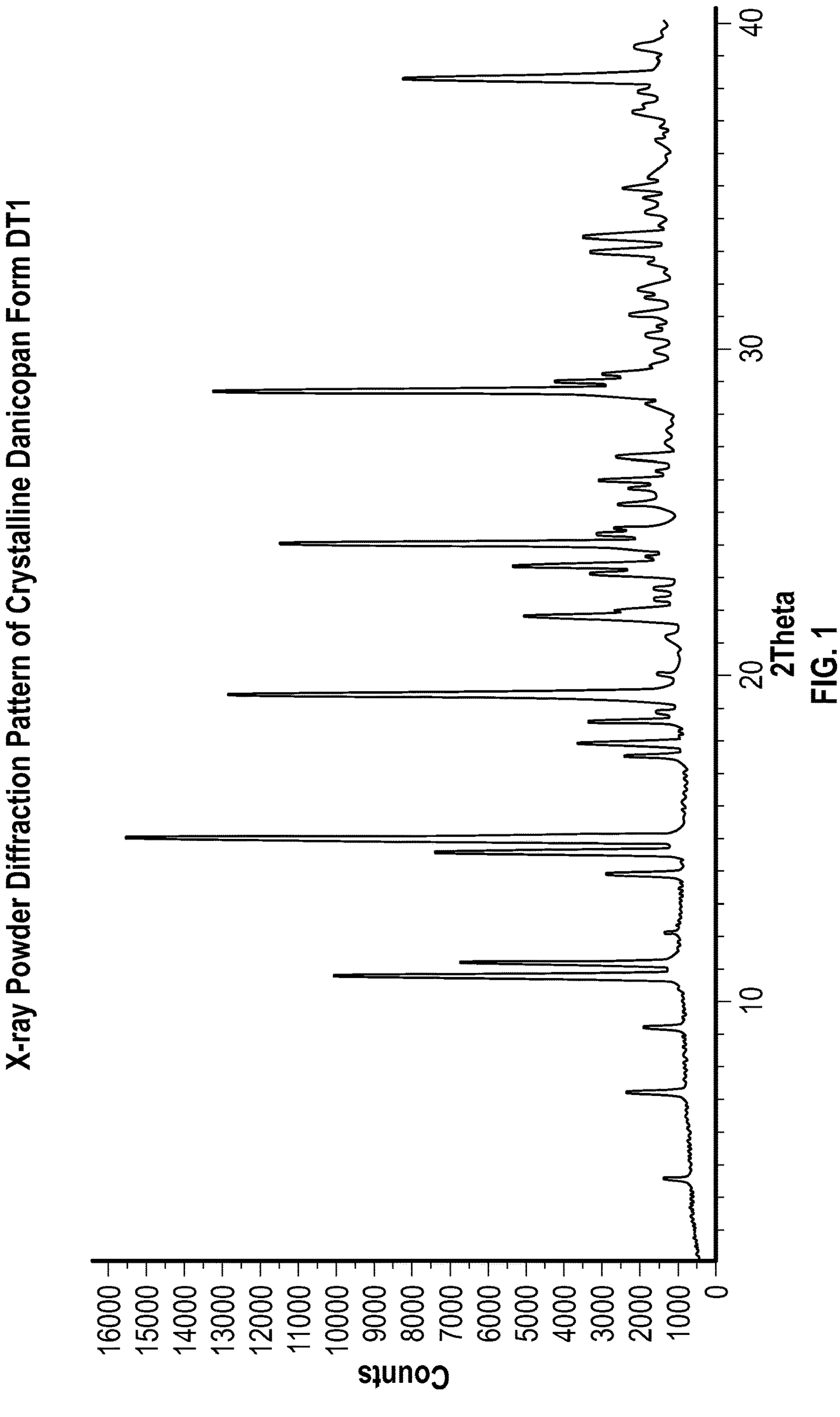
FIG. 1 shows an X-ray powder diffraction (XRPD) pattern for crystalline Danicopan Form DT1.

The present disclosure relates to solid state forms or crystalline polymorphs of Danicopan, to processes for preparation thereof and to pharmaceutical compositions comprising at least one of, or combination of these solid state forms. In particular, the present disclosure relates to solid state forms of Danicopan designated as Form DT1-Form DT6 (defined herein).

The Danicopan solid state forms, according to the present disclosure may have advantageous properties selected from at least one of: chemical or polymorphic purity, flowability, solubility, dissolution rate, bioavailability, morphology or crystal habit, stability—such as chemical stability as well as thermal and mechanical stability with respect to polymorphic conversion, stability towards dehydration and/or storage stability, a lower degree of hygroscopicity, low content of residual solvents, adhesive tendencies and advantageous processing and handling characteristics such as compressibility, and bulk density. Particularly, Danicopan Form DT2 has been shown to be particularly stable to high relative humidity, temperature and compression and hence represents an excellent candidate for incorporating into pharmaceutical compositions.

A crystal form may be referred to herein as being characterized by graphical data "as depicted in" a Figure. Such data include, for example, powder X-ray diffractograms and solid state NMR spectra. As is well-known in the art, the graphical data potentially provides additional technical information to further define the respective solid state form (a so-called "fingerprint") which can not necessarily be described by reference to numerical values or peak positions alone. In any event, the skilled person will understand that such graphical representations of data may be subject to small variations, e.g., in peak relative intensities and peak positions due to factors such as variations in instrument response and variations in sample concentration and purity, which are well known to the skilled person. Nonetheless, the skilled person would readily be capable of comparing the graphical data in the Figures herein with graphical data generated for an unknown crystal form and confirm whether the two sets of graphical data are characterizing the same crystal form or two different crystal forms.

A crystal form of Danicopan, referred to herein as being characterized by graphical data "as depicted in" a Figure will thus be understood to include any crystal form of Danicopan characterized with the graphical data having such small variations, as are well known to the skilled person, in comparison with the Figure.

The solid state forms or crystalline polymorphs of Danicopan as described in any aspect or embodiment of the present disclosure may be polymorphically pure, or substantially free of any other solid state forms of Danicopan.

A solid state form (or polymorph) may be referred to herein as polymorphically pure or as substantially free of any other solid state (or polymorphic) forms. As used herein in this context, the expression "substantially free of any other forms" will be understood to mean that the solid state form contains about 20% (w/w) or less, about 10% (w/w) or less, about 5% (w/w) or less, about 2% (w/w) or less, about 1% (w/w) or less, or about 0% (w/w) of any other forms of the subject compound as measured, for example, by XRPD. Thus, solid states of Danicopan described herein as substantially free of any other solid state forms would be understood to contain greater than about 80% (w/w), greater than about 90% (w/w), greater than about 95% (w/w), greater than about 98% (w/w), greater than about 99% (w/w), or about 100% of the subject solid state form of Danicopan. Accordingly, in some embodiments of the disclosure, the described solid state form of Danicopan may contain from about 1% to about 20% (w/w), from about 5% to about 20% (w/w), or from about 5% to about 10% (w/w) of one or more solid state forms of Danicopan.

The solid state forms or crystalline polymorphs of Danicopan as described in any aspect or embodiment of the present disclosure may be chemically pure, or substantially free of any other compounds.

A compound may be referred to herein as chemically pure or purified compound or as substantially free of any other compounds. As used herein, the terms “chemically pure” or “purified” or “substantially free of any other compounds” refer to a compound that is substantially free of any impurities including enantiomers of the subject compound, diastereomers or other isomers. A chemically pure or purified compound or a compound that is substantially free of any other compound will be understood to mean that it contains about 10% (w/w) or less, about 5% (w/w) or less, about 4% (w/w) or less, about 3% (w/w) or less, about 2% (w/w) or less, about 1.5% (w/w) or less, about 1% (w/w), about 0.8% (w/w) or less, about 0.6% (w/w) or less about 0.4% (w/w) or less about 0.2% (w/w) or less or less, about 0.1% (w/w) or less or about 0% of any other compound as measured, for example, by HPLC. Alternatively, A chemically pure or purified compound or a compound that is substantially free of any other compound will be understood to mean that it contains about 10% area percent or less, about 5% area percent or less, about 4% area percent or less, about 3% area percent or less, about 2% area percent or less, about 1.5% area percent or less, about 1% area percent or less, about 0.8% area percent or less, about 0.6% area percent or less, about 0.4% area percent or less, about 0.2% area percent or less, about 0.1% area percent or less, or about 0% of any other compound as measured by HPLC. Thus, pure or purified Danicopan described herein as substantially free of any compounds would be understood to contain greater than about 90% (w/w), greater than about 95% (w/w), greater than about 96% (w/w), greater than about 97% (w/w), greater than about 98% (w/w), greater than about 98.5% (w/w), greater than about 99% (w/w), greater than about 99.2%, (w/w) greater than about 99.4% (w/w), greater than about 99.6% (w/w), greater than about 99.8% (w/w), greater than about 99.9% (w/w), or about 100% of the subject Danicopan. Alternatively, pure or purified Danicopan described herein as substantially free of any compounds would be understood to contain greater than about 90% area percent, greater than about 95% area percent, greater than about 96% area percent, greater than about 97% area percent, greater than about 98% area percent, greater than about 98.5% area percent, greater than about 99% area percent, greater than about 99.2%, area percent, greater than about 99.4% area percent, greater than about 99.6% area percent, greater than about 99.8% area percent, greater than about 99.9% area percent, or about 100% of the subject Danicopan.

As used herein, unless stated otherwise, XRPD peaks reported herein are preferably measured using CuKα radiation, λ=1.5418 Å, preferably, XRPD peaks reported herein are measured using CuK α radiation, λ=1.5418 Å, at a temperature of 25±3° C.

As used herein, the term “isolated” in reference to solid state form of Danicopan of the present disclosure corresponds to solid state form of Danicopan that is physically separated from the reaction mixture in which it is formed.

A thing, e.g., a reaction mixture, may be characterized herein as being at, or allowed to come to “room temperature”, often abbreviated “RT.” This means that the temperature of the thing is close to, or the same as, that of the space, e.g., the room or fume hood, in which the thing is located. Typically, room temperature is from about 20° C. to about 30° C., or about 22° C. to about 27° C., or about 25° C.

A process or step may be referred to herein as being carried out “overnight.” This refers to a time interval, e.g., for the process or step, that spans the time during the night, when that process or step may not be actively observed. This time interval is from about 8 to about 20 hours, or about 10 to about 18 hours, typically about 16 hours.

As used herein, and unless stated otherwise, the term “anhydrous” in relation to crystalline Danicopan which does not include any crystalline water (or other solvents) in a defined, stoichiometric amount within the crystal. Moreover, an “anhydrous” form does not contain more than about 1% (w/w) of either water or organic solvents as measured for example by TGA, Karl Fischer or by other suitable technique.

The term “solvate”, as used herein and unless indicated otherwise, refers to a crystal form that incorporates a solvent in the crystal structure. When the solvent is water, the solvate is often referred to as a “hydrate.” The solvent in a solvate may be present in either a stoichiometric or in a non-stoichiometric amount.

The amount of solvent employed in a chemical process, e.g., a reaction or crystallization may be referred to herein as a number of “volumes” or “vol” or “V.” For example, a material may be referred to as being suspended in 10 volumes (or 10 vol or 10V) of a solvent. In this context, this expression would be understood to mean milliliters of the solvent per gram of the material being suspended, such that suspending a 5 grams of a material in 10 volumes of a solvent means that the solvent is used in an amount of 10 milliliters of the solvent per gram of the material that is being suspended or, in this example, 50 mL of the solvent. In another context, the term “v/v” may be used to indicate the number of volumes of a solvent that are added to a liquid mixture based on the volume of that mixture. For example, adding (methyl tert-butyl ether) MTBE (1.5 v/v) to a 100 ml reaction mixture would indicate that 150 mL of MTBE was added.

As used herein the term non-hygroscopic in relation to crystalline Danicopan, refers to less than about 1.0% (w/w) absorption of water at about 25° C. and about 80% relative humidity (RH), as determined for example by TGA or other suitable technique.

As used herein, the term “reduced pressure” refers to a pressure of about 10 mbar to about 500 mbar.

As used herein, and unless indicated otherwise, the term “thermo-dynamical stability” in relation to solid state forms or crystalline polymorphs of Danicopan refers to resistance of the solid state form or crystalline polymorph to polymorphic conversion under certain conditions, for example, heating, melting or dissolving. In some embodiments, the term refers to less than about 20% (w/w), about 10% (w/w), about 5% (w/w), about 1% (w/w), about 0.5% (w/w), or about 0% (w/w) conversion of crystalline Danicopan to any other solid state form of Danicopan as measured by XRPD. In some embodiments, the conversion is about 1% (w/w) to about 20% (w/w), about 1% (w/w) to about 10% (w/w) or about 1% (w/w) to about 5% (w/w).

The present disclosure comprises a crystalline Danicopan designated as Form DT1. Danicopan crystalline Form DTI can be characterized by data selected from one or more of the following: an XRPD pattern having peaks at 7.2, 11.2, 14.6, 19.5 and 28.7 degrees 2-theta±0.2 degrees 2-theta; an XRPD pattern substantially as depicted in FIG. 1; or combinations of these data.

Crystalline Danicopan Form DT1 may be further characterized by data selected from one or more of the following: an XRPD pattern having peaks at 7.2, 11.2, 14.6, 19.5 and 28.7 degrees two theta±0.2 degrees two theta; and also having one, two, three or four additional peaks selected from 10.8, 17.9, 21.8 and 24.0 degrees two theta±0.2 degrees two theta; or combinations of these data.

Crystalline Danicopan Form DT1 may alternatively be characterized by XRPD pattern having peaks at 7.2, 10.8, 11.2, 14.6, 17.9, 19.5, 21.8, 24.0 and 28.7 degrees two theta±0.2 degrees two theta.

Crystalline Danicopan Form DT1 may be characterized by each of the above characteristics alone/or by all possible combinations, e.g. by XRPD pattern having peaks at 7.2, 11.2, 14.6, 19.5 and 28.7 degrees two theta±0.2 degrees two theta and an XRPD pattern as depicted in FIG. 1, and combinations thereof.

Crystalline Danicopan Form DT1 may be characterized as vinyl acetate solvate, in embodiments a hemi vinyl acetate solvate. Typically, Danicopan Form DT1 may contain from about 3% to about 8% of vinyl acetate by weight, preferably from about 4% to about 7% by weight, more preferably from about 4% to about 6% by weight, or about 5.3% by weight, as determined for example by TGA or by other suitable techniques.

Figure 2:
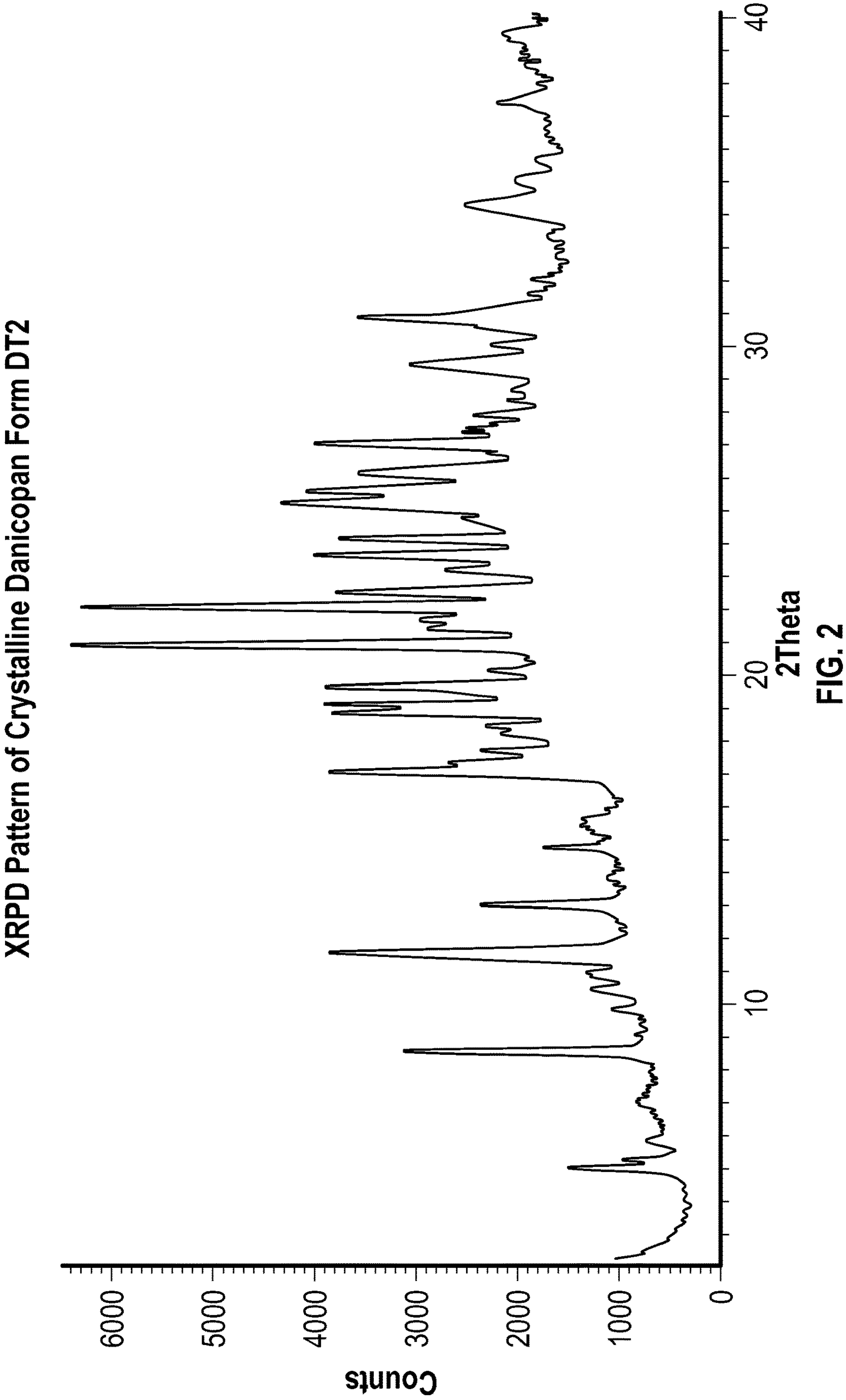
FIG. 2 shows an XRPD pattern of crystalline Danicopan Form DT2.
Figure 3:
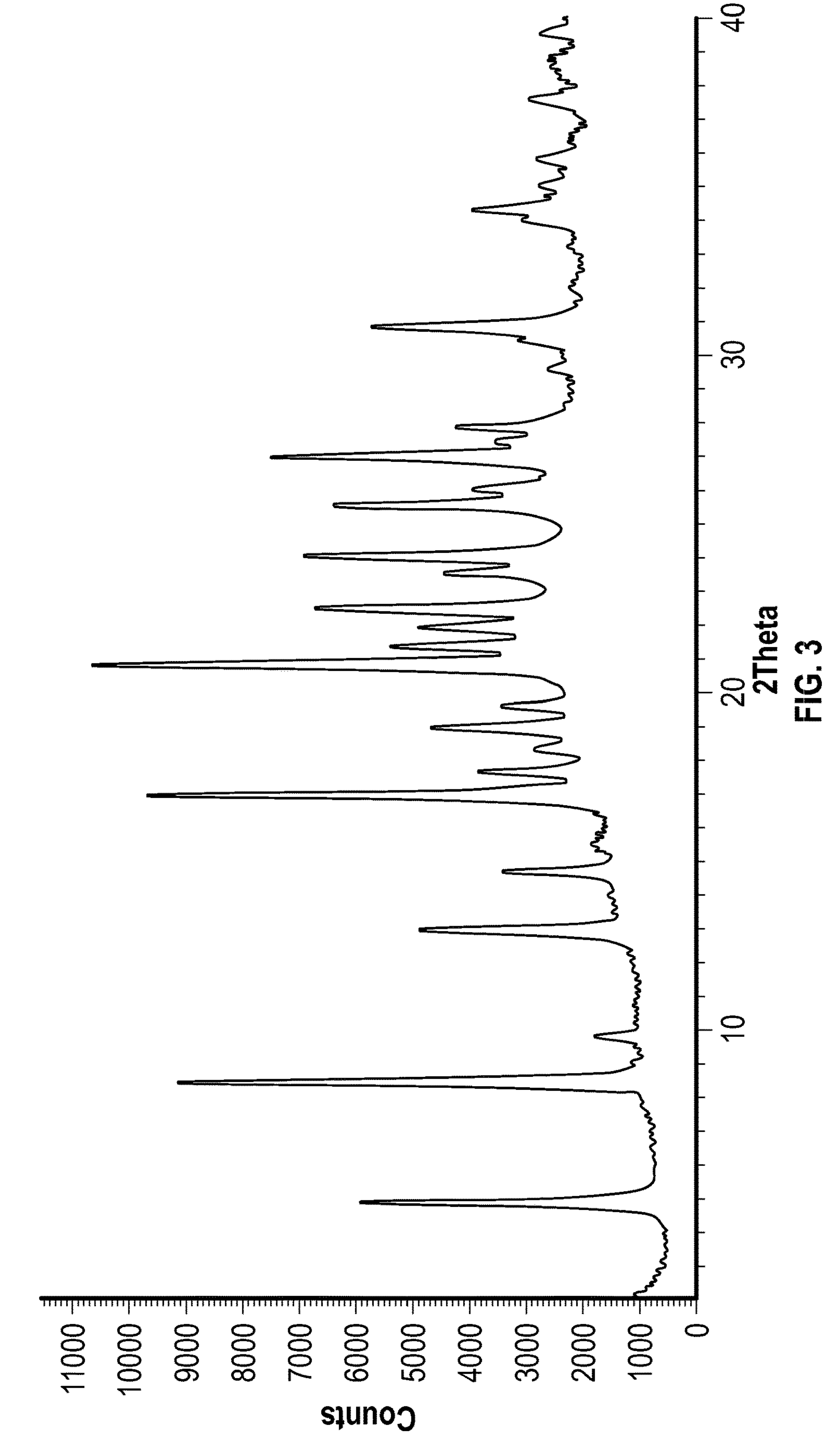
FIG. 3 shows an XRPD pattern of crystalline Danicopan pure Form DT2.

The present disclosure comprises a crystalline form of Danicopan designated as Form DT2. The crystalline Form DT2 of Danicopan can be characterized by data selected from one or more of the following: an XRPD pattern having peaks at 8.5, 12.9, 14.7, 17.0 and 19.6 degrees 2-theta±0.2 degrees 2-theta; an XRPD pattern substantially as depicted in FIG. 2; an XRPD pattern substantially as depicted in FIG. 3; or combinations of these data.

Crystalline Danicopan Form DT2 may be further characterized by data selected from one or more of the following: an XRPD pattern having peaks at 8.5, 12.9, 14.7, 17.0 and 19.6 degrees two theta±0.2 degrees two theta; and also having one, two, three or four additional peaks selected from 11.5, 22.0, 22.5 and 30.9 degrees two theta±0.2 degrees two theta; or combinations of these data.

Crystalline Danicopan Form DT2 may be further characterized by data selected from one or more of the following: an XRPD pattern having peaks at 8.5, 12.9, 14.7, 17.0 and 19.6 degrees two theta±0.2 degrees two theta; and also having one, two, three or four additional peaks selected from 20.9, 22.0, 22.5, 27.0 and 30.9 degrees two theta±0.2 degrees two theta; or combinations of these data. Crystalline Danicopan Form DT2 may be alternatively characterized by data selected from one or more of the following: an XRPD pattern having peaks at 8.5, 12.9, 14.7, 17.0 and 19.6 degrees two theta±0.2 degrees two theta; and also having one, two, three, four, or five additional peaks selected from 20.9, 22.0, 22.5, 27.0 and 30.9 degrees two theta±0.2 degrees two theta; or combinations of these data.

Crystalline Danicopan Form DT2 my alternatively be characterized by XRPD pattern having peaks at 8.5, 12.9, 14.7, 17.0, 19.6, 20.9, 22.0, 22.5, 27.0 and 30.9 degrees two theta±0.2 degrees two theta.

Crystalline Danicopan Form DT2 may alternatively be characterized by XRPD pattern having peaks at 8.5, 11.5, 12.9, 14.7, 17.0, 19.6, 22.0, 22.5 and 30.9 degrees two theta±0.2 degrees two theta.

Crystalline Danicopan Form DT2 may be characterized by each of the above characteristics alone/or by all possible combinations, e.g. by XRPD pattern having peaks at 8.5, 12.9, 14.7, 17.0 and 19.6 degrees two theta±0.2 degrees two theta; an XRPD pattern as depicted in FIG. 2, an XRPD pattern as depicted in FIG. 3, and combinations thereof.

Crystalline Danicopan Form DT2 may be anhydrous form.

According to any aspect or embodiment of the present disclosure, Danicopan Form DT2 is preferably an anhydrous form.

In another embodiment of the present disclosure, Danicopan Form DT2 is polymorphically pure. Optionally, according to any aspect or embodiment of the present disclosure, Danicopan Form DT2 may contain: about 20% (w/w) or less, about 10% (w/w) or less, about 5% (w/w) or less, about 2% (w/w) or less, about 1% (w/w) or less, about 0.5% (w/w) or less, or about 0% (i.e. undetectable levels) of any other solid state forms of Danicopan as measured, for example, by XRPD.

As discussed above, depending on which other solid state it is compared with, Danicopan Form DT2, according to the present disclosure may have advantageous properties as described above. Danicopan Form DT2 may in particular show higher solubility, stability or other improved physical properties compared to other known crystalline polymorphs of Danicopan.

Danicopan Form DT2 according to any aspect or embodiment of the present disclosure can be prepared by process suspending Danicopan form DTI as described herein, in a solvent under heating. The solvent is preferably a hydrocarbon, and more particularly a $C_5$ to $C_{10}$ hydrocarbon, particularly: a $C_5$ to $C_{10}$ alkane, a $C_5$ to $C_{10}$ cycloalkane, or a $C_6$ to $C_{10}$—aromatic hydrocarbon or a mixture thereof. More preferably, the solvent is a $C_5$ to Ca alkane, $C_5$ to $C_8$ cycloalkane, or a $C_6$ to $C_8$ aromatic hydrocarbon. Even more preferably, the solvent is a $C_5$ to $C_6$ alkane, a $C_5$ to $C_6$ alkane, or a $C_6$ to $C_7$ aromatic hydrocarbon. Particularly, the solvent may be selected from cyclopentane, cyclohexane, n-heptane, and hexane, and especially n-heptane or cyclohexane. The solvent may be used in an amount of: about 20 vol to about 160 vol, about 30 vol to about 150 vol, or about 40 vol to about 140 vol, about 50 vol to about 135 vol, about 65 vol to about 130 vol or about 70 vol to about 125 vol relative to Danicopan. In any embodiment of this process, the solvent may be n-heptane, which is preferably used in an amount of: about 80 vol to about 150 vol, or about 90 vol to about 140 vol, about 100 vol to about 130 vol, about 110 vol to about 130 vol, about 115 vol to about 125 vol relative to Danicopan. Alternatively, the solvent may be cyclohexane, which is preferably used in an amount of: about 40 vol to about 100 vol, or about 50 vol to about 95 vol, about 60 vol to about 90 vol, about 65 vol to about 85 vol, about 70 vol to about 80, or about 75 vol relative to Danicopan.

Preferably, the suspension is heated to about 40° C. to about 100° C., about 45° C. to about 90° C., or about 45° C. about 80° C., about 50° C. to about 70° C., about 55° C. to about 65° C., or about 60° C. The mixture may be stirred for any suitable time to prepare Form DT2, preferably for about 12 hours to about 120 hours, about 20 hours to about 100 hours, about 30 hours to about 80 hours, or about 40 hours to about 75 hours. The mixture may be cooled, preferably to a temperature of about 15° C. to about 35° C., about 20° C. to about 35° C. or about 25° C., preferably over a period of: about 30 min to 120 min, preferably 60 min.

Form DT2 may be isolated by any suitable method, such as by centrifuge, by decantation or by filtration, preferably by filtration. Preferably, the filtration is carried out at temperature of about 10° C. to about 40° C., preferably about 20° C. to about 30° C. Following the isolation, the product may be washed, and optionally dried. Drying may be done by nitrogen or air or under vacuum. Drying may be performed at a temperature of about 50° C. to about 70° C., in embodiment about 60° C., preferably for a period of: about 2 to about 18 hours, about 2 to about 15 hours, about 4 to about 10 hours, about 4 to about 8 hours, or about 6. When the drying is carried out under vacuum, a reduced pressure of: about 1 or about 200 mbar, about 1 to about 100 mbar, about 1 to about 50 mbar, and particularly about 5 to about 40 mbar or more particularly, about 20 mbar, may be used.

The above Danicopan Form DT2 can be prepared by process combining suspending amorphous Danicopan in n-heptane under heating.

Typically, n-heptane, may be used in an amount of: about 20 vol to about 140 vol, about 20 vol to about 80 vol, or about 20 vol to about 40 vol, or about 24 vol relative to Danicopan.

Preferably, the slurry mixture is heated to about 40° C. to about 100° C., about 50° C. to about 90° C., or about 60° C. about 90° C., about 60° C. to about 80° C., or about 60° C. to about 70° C. The mixture may be stirred for any suitable time to prepare Form DT2, preferably for about 12 hours to about 72 hours, about 18 hours to about 64 hours, about 12 hours to about 48 hours, or about 24 hours. The mixture may be cooled, preferably to a temperature of about 15° C. to about 35° C., about 20° C. to about 35° C. or about 25° C., preferably over a period of: about 30 min to 120 min, preferably 60 min.

Form DT2 may be isolated by any suitable method, such as by centrifuge, by decantation or by filtration, preferably by filtration. Preferably, the filtration is carried out at temperature of about 10° C. to about 40° C., preferably about 20° C. to about 30° C. Following the isolation, the product may be washed, and optionally dried. Drying may be done by nitrogen or air or under vacuum. Drying may be performed at a temperature of about 50° C. to about 70° C., in embodiment about 60° C., preferably for about 4 to 48 hours, in embodiment 24 hours. When the drying is carried out under vacuum, a reduced pressure of: about 1 or about 200 mbar, about 1 to about 100 mbar, about 1 to about 50 mbar, and particularly about 5 to about 40 mbar or more particularly, about 20 mbar, may be used.

Danicopan Form DT2 as described in any aspect or embodiment of the present disclosure can be prepared by a process comprising:

a) combining a solution of Danicopan in a solvent; particularly wherein the solvent is an organic carbonate (preferably a $C_3$ to $C_8$ organic carbonate, particularly a dialkylcarbonate, a di($C_1$-$C_3$) alkylcarbonate wherein the alkyl groups can be the same or different, or dimethylcarbonate, diethylcarbonate, or methylethylcarbonate, and especially diethylcarbonate), or wherein the solvent is a ketone [preferably a $C_3$ to $C_8$ ketone, particularly a di($C_1$-$C_3$ alkyl) ketone wherein the alkyl groups can be the same or different, or acetone, diethylketone (3-pentanone), or methylethylketone), and especially diethylketone];

b) optionally isolating Danicopan Form DT2; and c) optionally drying.

Danicopan used in step (a) may be crystalline or amorphous, preferably amorphous Danicopan.

In any aspect or embodiment of the above processes, the solvent in step (a) is selected from ketones (such as a $C_3$-$C_6$ ketone) or organic carbonates (such as $C_3$-$C_6$ linear or cyclic carbonates) or a combination thereof; According to any embodiment of the process, the ketone in step (a) is selected from: acetone, diethyl ketone (3-pentanone), methyl isobutyl ketone, preferably diethyl ketone and the carbonate is selected from diethyl carbonate, dimethyl carbonate, ethylene carbonate, preferably diethyl carbonate.

In any aspect or embodiment of the above processes for preparing Danicopan Form DT2, about 3 vol to about 10 vol, about 4 to about 7 vol, about 4 to about 6 vol, or about 5 vol is used to dissolve Danicopan.

In any aspect or embodiment of the above processes, the solution of Danicopan may be heated to a temperature of about 40° C. to about 100° C., in embodiments about 50° C. to about 80° C., and in other embodiments to about 60° C., preferably with stirring. In embodiments, Danicopan solution is cooled to a temperature of: about 40° C. to about 20° C., or about 30° C. to about 20° C., or about 25° C., optionally cooling in about 30 min to 2 hours, preferably in 1 hour.

In any embodiment of the above processes for preparing Form DT2, step (b) may include isolation of Danicopan Form DT2. The isolation may be carried out by any suitable means, such as by centrifuge, decantation, or by filtration, preferably by filtration. Preferably, the filtration is carried out at temperature of about 10° C. to about 40° C., preferably about 20° C. to about 30° C. Following the isolation, the product may be washed, and optionally dried. Drying may be done by nitrogen or air or under vacuum. Drying may be performed at a temperature of about 30° C. to about 80° C., or about 60° C., preferably for about 1 to 24 hours, in embodiment 6 hours. When the drying is carried out under vacuum, a reduced pressure of: about 1 or about 200 mbar, about 1 to about 100 mbar, about 1 to about 50 mbar, and particularly about 5 to about 40 mbar or more particularly, about 20 mbar, may be used.

The above described processes for preparing Form DT2 of Danicopan may further comprise combining the Form DT2 of Danicopan with at least one pharmaceutically acceptable excipient to prepare a pharmaceutical formulation or dosage form.

Figure 4:
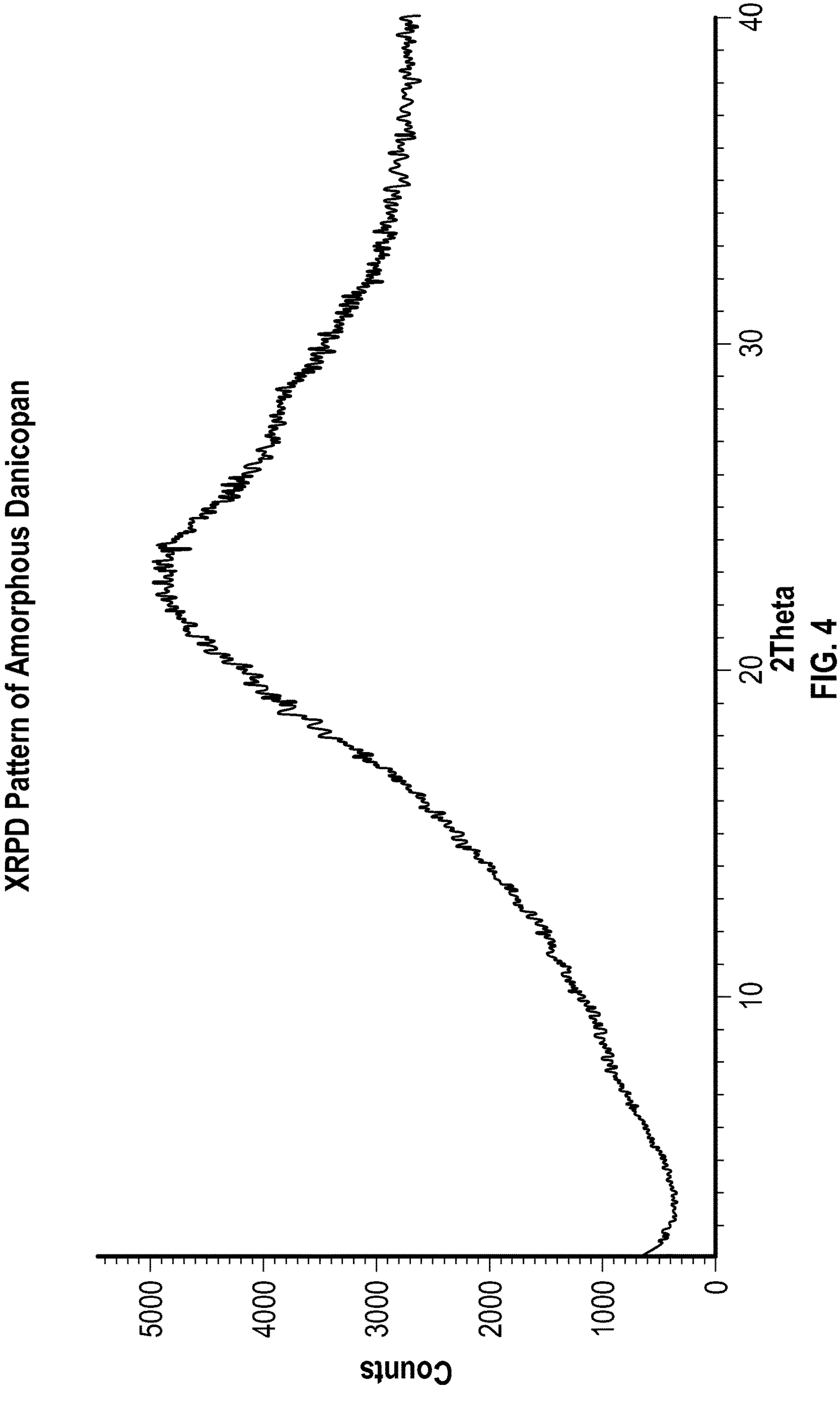
FIG. 4 shows an XRPD pattern of Amorphous Danicopan.

The present disclosure comprises Amorphous Danicopan. Amorphous Danicopan can be characterized by data selected from one or more of the following: an XRPD pattern which does not include any crystalline peak; an XRPD pattern substantially as depicted in FIG. 4; or combinations of these data.

The present disclosure comprises a crystalline Danicopan designated as Form DT3. Danicopan crystalline Form DT3 can be characterized by data selected from one or more of the following: an XRPD pattern having peaks at 12.3, 12.9, 13.7, 21.0 and 22.3 degrees 2-theta±0.2 degrees 2-theta; an XRPD pattern substantially as depicted in FIG. 5; or combinations of these data.

Crystalline Danicopan Form DT3 may be further characterized by data selected from one or more of the following: an XRPD pattern having peaks at 12.3, 12.9, 13.7, 21.0 and 22.3 degrees two theta±0.2 degrees two theta; and also having one, two, three or four additional peaks selected from 10.4, 16.6, 24.1 and 26.1 degrees two theta±0.2 degrees two theta; or combinations of these data.

Crystalline Danicopan Form DT3 may alternatively be characterized by XRPD pattern having peaks at 10.4, 12.3, 12.9, 13.7, 16.6, 21.0, 22.3, 24.1 and 26.1 degrees two theta±0.2 degrees two theta.

Figure 5:
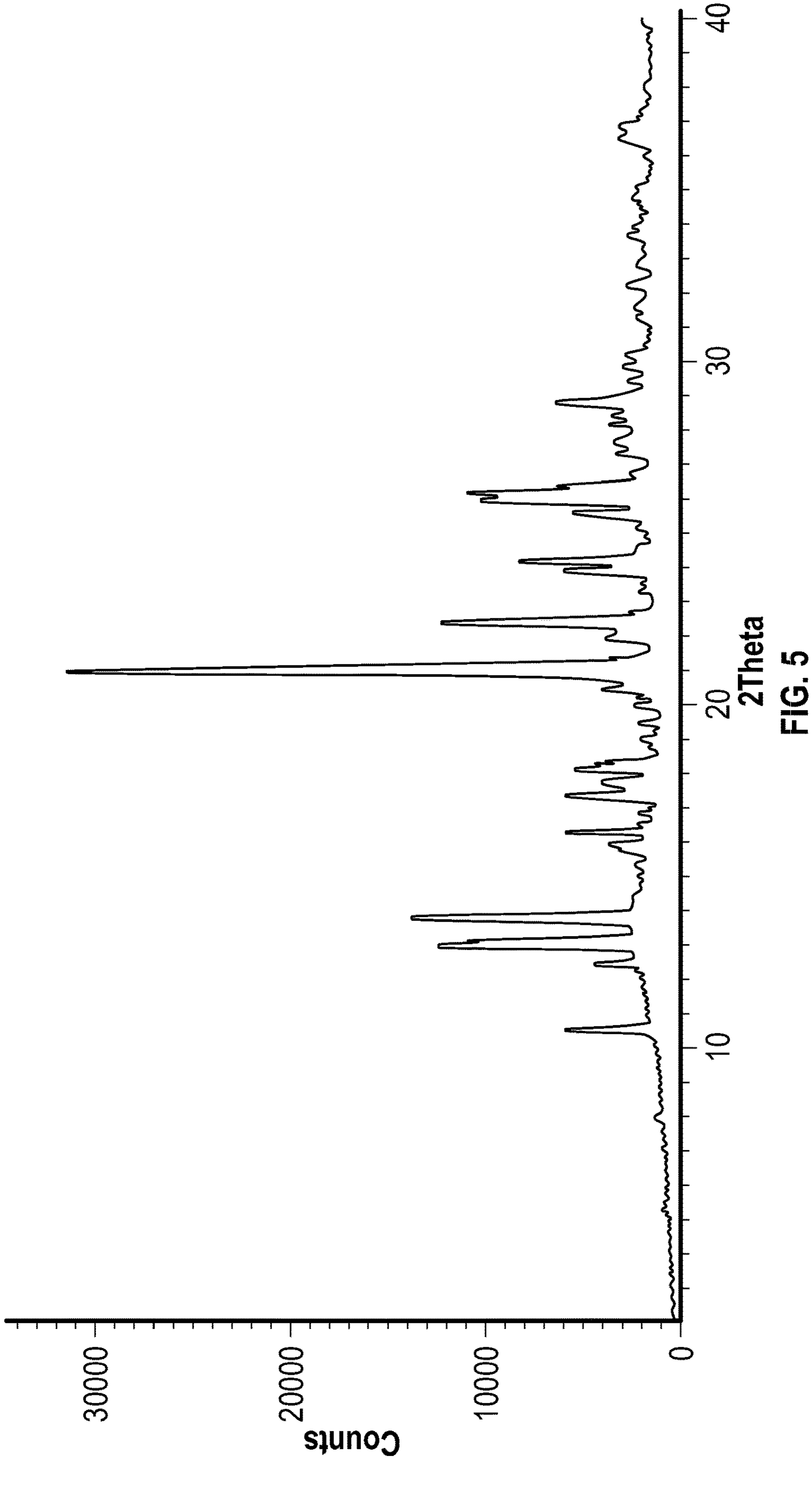
FIG. 5 shows an XRPD pattern of crystalline Danicopan Form DT3.

Crystalline Danicopan Form DT3 may be characterized by each of the above characteristics alone/or by all possible combinations, e.g. by XRPD pattern having peaks at 12.3, 12.9, 13.7, 21.0 and 22.3 degrees two theta±0.2 degrees two theta and an XRPD pattern as depicted in FIG. 5, and combinations thereof.

Crystalline Danicopan Form DT3 may be characterized as Dimethylacetamide solvate, in embodiments crus di-dimethylacetamide solvate. Typically, Danicopan Form DT3 may contain from about 15% to about 25% of dimethylacetamide by weight, preferably from about 18% to about 23% by weight, or about 21.9% by weight, as determined for example by TGA or by other suitable techniques.

The present disclosure comprises a crystalline Danicopan designated as Form DT4. Danicopan crystalline Form DT4 can be characterized by data selected from one or more of the following: an XRPD pattern having peaks at 8.0, 10.8, 12.8, 20.6, 24.2 and 25.2 degrees 2-theta±0.2 degrees 2-theta; an XRPD pattern substantially as depicted in FIG. 6; or combinations of these data.

Crystalline Danicopan Form DT4 may be further characterized by data selected from one or more of the following: an XRPD pattern having peaks at 8.0, 10.8, 12.8, 20.6, 24.2 and 25.2 degrees two theta±0.2 degrees two theta; and also having one, two, three or four additional peaks selected from 15.7, 19.3, 19.8 and 23.3 degrees two theta±0.2 degrees two theta; or combinations of these data.

Crystalline Danicopan Form DT4 may alternatively be characterized by XRPD pattern having peaks at 8.0, 10.8, 12.8, 15.7, 19.3, 19.8, 20.6, 23.3, 24.2 and 25.2 degrees two theta±0.2 degrees two theta.

Figure 6:
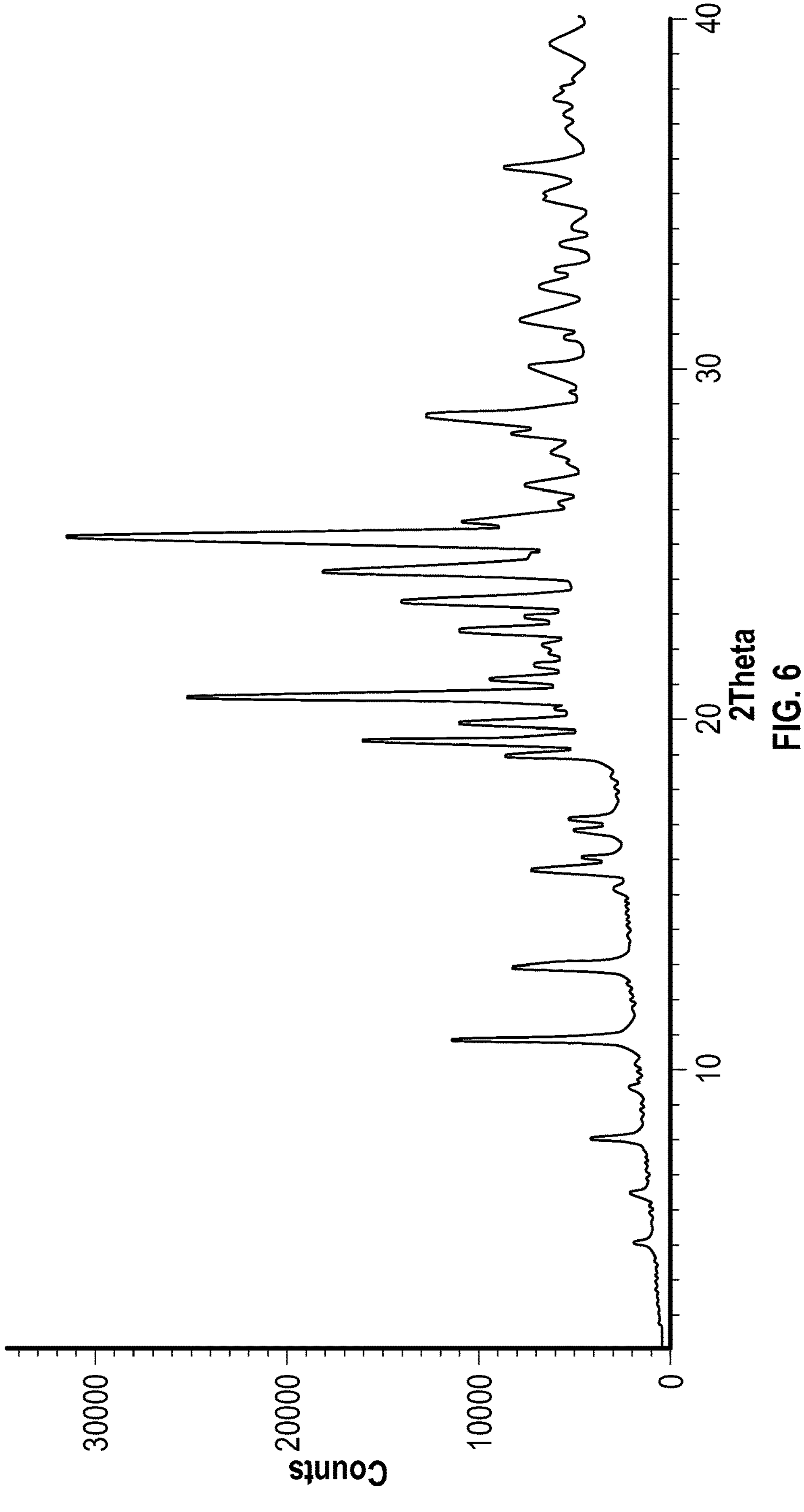
FIG. 6 shows an XRPD pattern of crystalline Danicopan Form DT4.

Crystalline Danicopan Form DT4 may be characterized by each of the above characteristics alone/or by all possible combinations, e.g. by XRPD pattern having peaks at 8.0, 10.8, 12.8, 20.6, 24.2 and 25.2 degrees two theta±0.2 degrees two theta and an XRPD pattern as depicted in FIG. 6, and combinations thereof.

Crystalline Danicopan Form DT4 may be characterized as Dimethylformamide (DMF) solvate, in embodiment di-DMF solvate. Typically, Danicopan Form DT4 may contain from about 15% to about 25% of DMF by weight, preferably from about 18% to about 23% by weight, or about 21.1% by weight, as determined for example by TGA or by other suitable techniques.

The present disclosure comprises a crystalline Danicopan designated as Form DT5. Danicopan crystalline Form DT5 can be characterized by data selected from one or more of the following: an XRPD pattern having peaks at 13.9, 17.3, 17.9, 24.0 and 24.8 degrees 2-theta±0.2 degrees 2-theta; an XRPD pattern substantially as depicted in FIG. 7; or combinations of these data.

Crystalline Danicopan Form DT5 may be further characterized by data selected from one or more of the following: an XRPD pattern having peaks at 13.9, 17.3, 17.9, 24.0 and 24.8 degrees two theta±0.2 degrees two theta; and also having one, two, three or four additional peaks selected from 6.9, 16.8, 18.9 and 26.7 degrees two theta±0.2 degrees two theta; or combinations of these data.

Crystalline Danicopan Form DT5 may alternatively be characterized by XRPD pattern having peaks at 6.9, 13.9, 16.8, 17.3, 17.9, 18.9, 24.0, 24.8 and 26.7 degrees two theta±0.2 degrees two theta.

Figure 7:
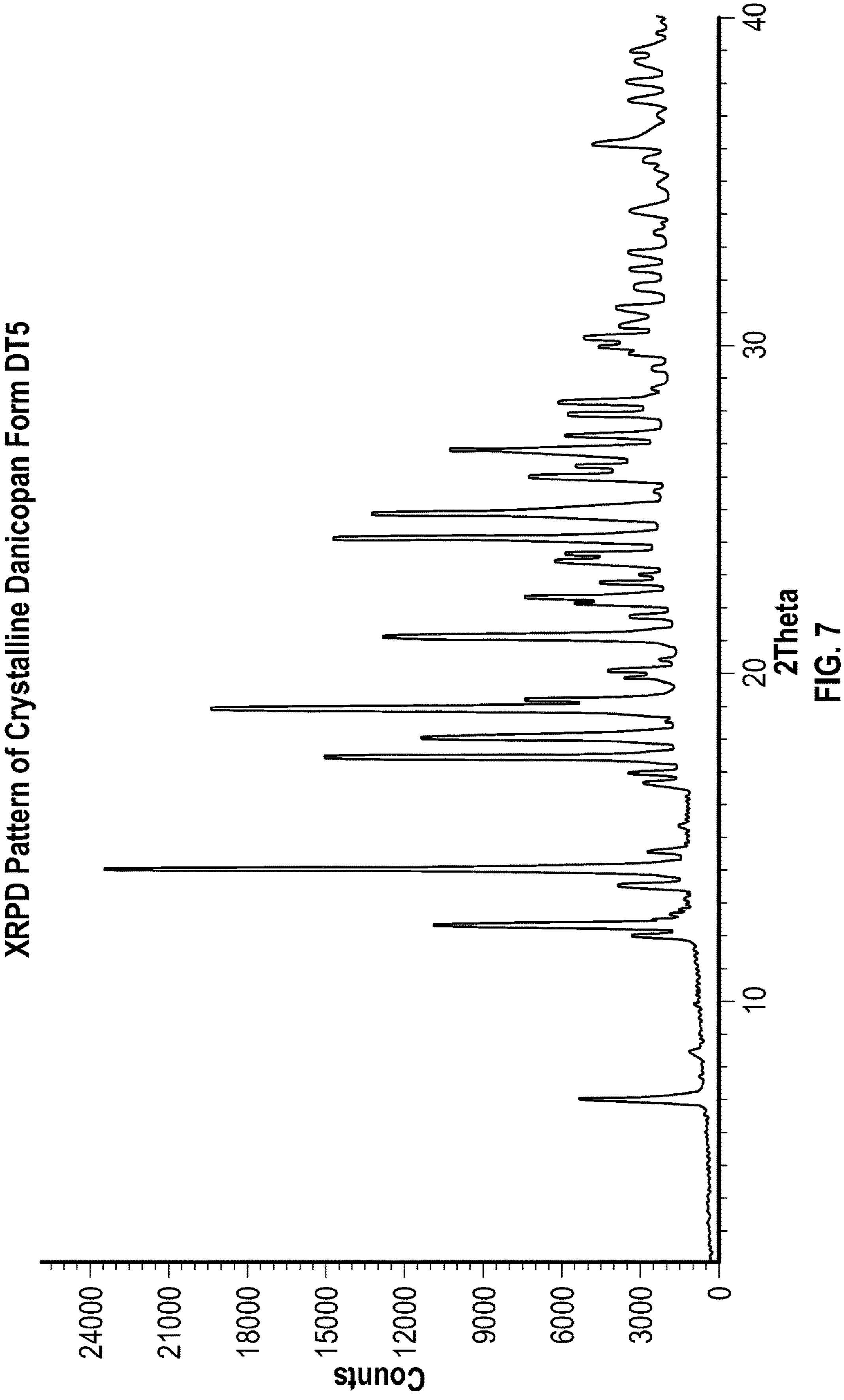
FIG. 7 shows an XRPD pattern of crystalline Danicopan Form DT5.

Crystalline Danicopan Form DT5 may be characterized by each of the above characteristics alone/or by all possible combinations, e.g. by XRPD pattern having peaks at 13.9, 17.3, 17.9, 24.0 and 24.8 degrees two theta±0.2 degrees two theta and an XRPD pattern as depicted in FIG. 7, and combinations thereof.

Crystalline Danicopan Form DT5 may be characterized as propionic acid solvate, preferably hemi propionic acid solvate. Typically, Danicopan Form DT5 may contain from about 2% to about 10% of propionic acid by weight, preferably from about 5% to about 8% by weight, or about 6.7% by weight, as determined for example by TGA or by other suitable techniques.

The present disclosure comprises a crystalline Danicopan designated as Form DT6. Danicopan crystalline Form DT6 can be characterized by data selected from one or more of the following: an XRPD pattern having peaks at 10.6, 12.0, 18.2, 21.5 and 25.7 degrees 2-theta±0.2 degrees 2-theta; an XRPD pattern substantially as depicted in FIG. 8; or combinations of these data.

Crystalline Danicopan Form DT6 may be further characterized by data selected from one or more of the following: an XRPD pattern having peaks at 10.6, 12.0, 18.2, 21.5 and 25.7 degrees two theta±0.2 degrees two theta; and also having one, two, three or four additional peaks selected from 7.2, 14.7, 17.3 and 27.9 degrees two theta±0.2 degrees two theta; or combinations of these data.

Crystalline Danicopan Form DT6 may alternatively be characterized by XRPD pattern having peaks at 7.2, 10.6, 12.0, 14.7, 17.3, 18.2 21.5, 25.7 and 27.9 degrees two theta±0.2 degrees two theta.

Figure 8:
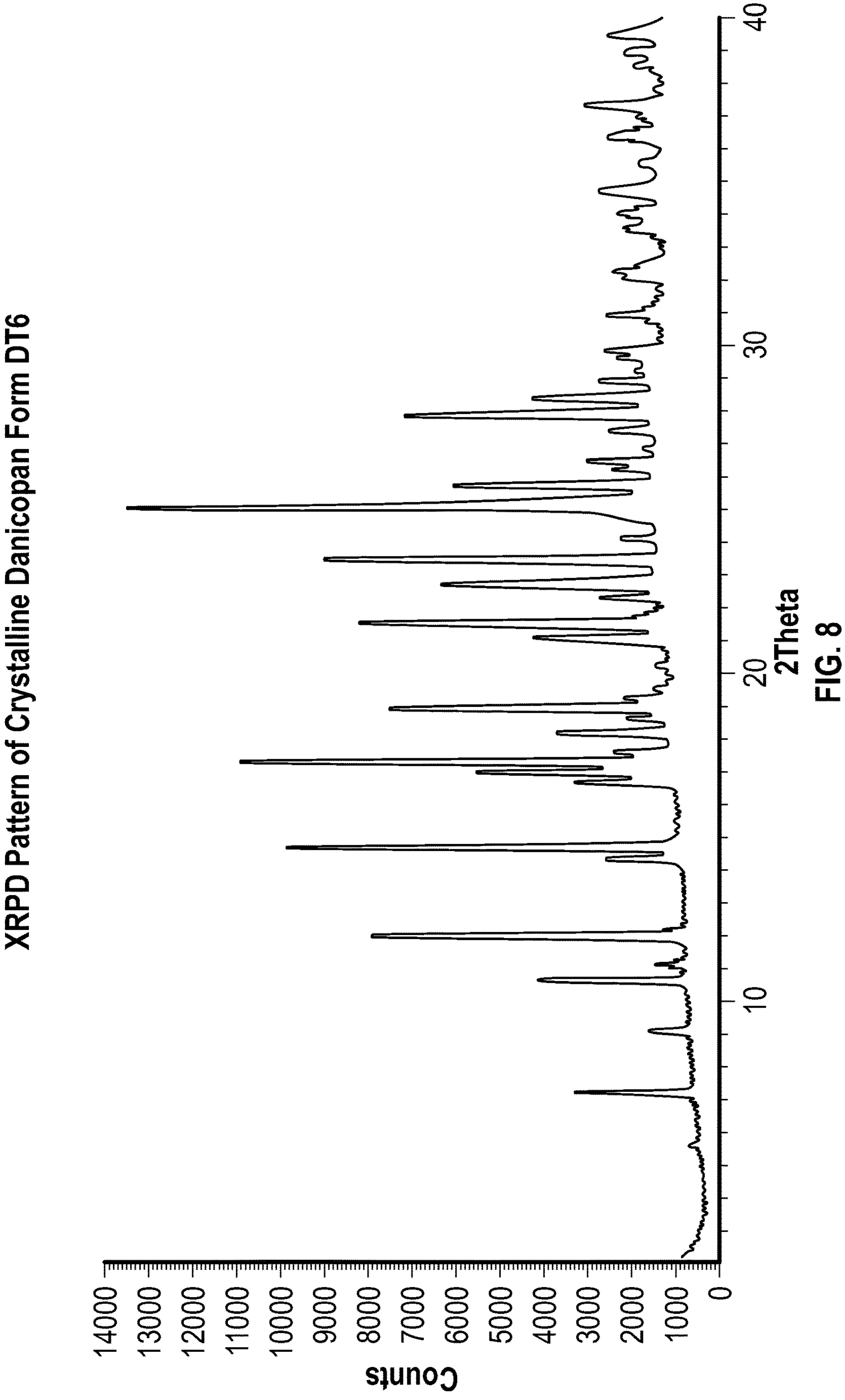
FIG. 8 shows an XRPD pattern of crystalline Danicopan Form DT6.

Crystalline Danicopan Form DT6 may be characterized by each of the above characteristics alone/or by all possible combinations, e.g. by XRPD pattern having peaks at 10.6, 12.0, 18.2, 21.5 and 25.7 degrees two theta±0.2 degrees two theta and an XRPD pattern as depicted in FIG. 8, and combinations thereof.

Crystalline Danicopan Form DT6 may be characterized as acetophenone solvate, in embodiment mono acetophenone solvate. Typically, Danicopan Form DT6 may contain from about 10% to about 20% of acetophenone by weight, preferably from about 15% to about 18% by weight, or about 16.5% by weight, as determined for example by TGA or by other suitable techniques.

In any aspect or embodiment of the present invention, crystalline Danicopan Forms DT1-DT6 described herein may be substantially free of any other solid state forms of Danicopan. Preferably, crystalline Forms DT1-DT6 of Danicopan according to any aspect or embodiment of the present invention contains about 20% (w/w) or less, about 10% (w/w) or less, about 5% (w/w) or less, about 2% (w/w) or less, about 1% (w/w) or less, about 0.5% (w/w), about 0.2% (w/w) or less, or about 0% (w/w) of any other forms of Danicopan as measured, for example, by XRPD. Thus, according to any aspect or embodiment of the present invention, the crystalline form comprises greater than about 80% (w/w), greater than about 90% (w/w), greater than about 95% (w/w), greater than about 98% (w/w), greater than about 99% (w/w), or about 100% of Forms DT1-DT6 of Danicopan. Preferably, crystalline Danicopan Forms DT1-DT6 according to any aspect or embodiment of the present invention contains no detectable amounts of other solid state forms of Danicopan (preferably as measured by XRPD).

In another embodiment of the present disclosure, crystalline Danicopan Forms DT1-DT6 are polymorphically pure.

In another embodiment of the present disclosure, crystalline Danicopan Form DT1-DT6 are isolated.

As described above, depending on which other solid state it is compared with, Danicopan Forms DT1-DT6 according to the present disclosure may have advantageous properties as described above.

The present disclosure also relates to a crystalline forms of Danicopan Forms DT1-DT6 which is obtainable by any process as described herein. The said process can include the process set out in the examples herein below.

The present disclosure also relates to a pharmaceutical composition comprising crystalline Danicopan Forms DT1-DT6 as described herein, or crystalline Danicopan Forms DT1-DT6 which is obtainable by any process as described herein below.

The invention further comprises a process for preparing a pharmaceutical composition comprising crystalline Danicopan Forms DT1-DT6, wherein the process comprises combining crystalline Danicopan Forms DT1-DT6 with at least one pharmaceutically acceptable excipient. The invention further comprises a process for preparing crystalline Danicopan Forms DT1-DT6 as described herein below and further comprising combining crystalline Danicopan Forms DT1-DT6 with at least one pharmaceutically acceptable excipient.

The present disclosure also provides for processes for the preparation of the solid state form of Danicopan. The said process can include the process set out in the examples herein below.

In another aspect, the present disclosure encompasses the above described solid state form of Danicopan for use in the preparation of pharmaceutical compositions and/or formulations, preferably for use in medicine, preferably for treating complement mediated diseases, preferably for the treatment of patients with paroxysmal nocturnal hemoglobinuria (PNH), optionally as an add-on therapy to a component 5 inhibitor, particularly wherein the component 5 inhibitor is ravulizumab or eculizumab, or for the treatment of geographic atrophy in age-related macular degeneration.

In another aspect, the present disclosure encompasses the use of the above described solid state form of Danicopan for the preparation of pharmaceutical compositions and/or formulations, preferably for use in medicine, preferably for treating complement mediated diseases, preferably for the treatment of patients with paroxysmal nocturnal hemoglobinuria (PNH), optionally as an add-on therapy to a component 5 inhibitor, particularly wherein the component 5 inhibitor is ravulizumab or eculizumab, or for the treatment of geographic atrophy in age-related macular degeneration.

In yet another embodiment, the present disclosure encompasses pharmaceutical compositions comprising the solid state form of Danicopan.

In specific embodiment, the present disclosure encompasses pharmaceutical formulation comprising the solid state form of Danicopan, and at least one pharmaceutically acceptable excipient.

The present disclosure further encompasses processes to prepare said pharmaceutical formulations of Danicopan, comprising combining the above described solid state form of Danicopan, or pharmaceutical compositions comprising them, and at least one pharmaceutically acceptable excipient.

The present disclosure comprises processes for preparing the above mentioned pharmaceutical compositions. The processes comprise combining the above crystalline polymorph of Danicopan, of the present disclosure with at least one pharmaceutically acceptable excipient.

Pharmaceutical formulations of the present invention contain the crystalline polymorph of Danicopan of the present invention, particularly crystalline Danicopan Forms DT1-DT6. In addition to the active ingredient, the pharmaceutical formulations of the present invention can contain one or more excipients. Excipients are added to the formulation for a variety of purposes.

Diluents increase the bulk of a solid pharmaceutical composition, and can make a pharmaceutical dosage form containing the composition easier for the patient and caregiver to handle. Diluents for solid compositions include, for example, microcrystalline cellulose (e.g. Avicel®), microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g. Eudragit®), potassium chloride, powdered cellulose, sodium chloride, sorbitol, and talc.

Solid pharmaceutical compositions that are compacted into a dosage form, such as a tablet, can include excipients whose functions include helping to bind the active ingredient and other excipients together after compression. Binders for solid pharmaceutical compositions include acacia, alginic acid, carbomer (e.g. carbopol), carboxymethylcellulose sodium, dextrin, ethyl cellulose, gelatin, guar gum, hydrogenated vegetable oil, hydroxyethyl cellulose, hydroxypropyl cellulose (e.g. Klucel®), hydroxypropyl methyl cellulose (e.g. Methocel®), liquid glucose, magnesium aluminum silicate, maltodextrin, methylcellulose, polymethacrylates, povidone (e.g. Kollidon®, Plasdone®), pregelatinized starch, sodium alginate, and starch.

The dissolution rate of a compacted solid pharmaceutical composition in the patient's stomach can be increased by the addition of a disintegrant to the composition Disintegrants include alginic acid, carboxymethylcellulose calcium, carboxymethylcellulose sodium (e.g. Ac-Di-Sol®, Primellose®), colloidal silicon dioxide, croscarmellose sodium, crospovidone (e.g. Kollidon®, Polyplasdone®), guar gum, magnesium aluminum silicate, methyl cellulose, microcrystalline cellulose, polacrilin potassium, powdered cellulose, pregelatinized starch, sodium alginate, sodium starch glycolate (e.g. Explotab®), and starch.

Glidants can be added to improve the flowability of a non-compacted solid composition and to improve the accuracy of dosing. Excipients that can function as glidants include colloidal silicon dioxide, magnesium trisilicate, powdered cellulose, starch, talc, and tribasic calcium phosphate.

When a dosage form such as a tablet is made by the compaction of a powdered composition, the composition is subjected to pressure from a punch and dye. Some excipients and active ingredients have a tendency to adhere to the surfaces of the punch and dye, which can cause the product to have pitting and other surface irregularities. A lubricant can be added to the composition to reduce adhesion and ease the release of the product from the dye. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc, and zinc stearate.

Flavoring agents and flavor enhancers make the dosage form more palatable to the patient. Common flavoring agents and flavor enhancers for pharmaceutical products that can be included in the composition of the present invention include maltol, vanillin, ethyl vanillin, menthol, citric acid, fumaric acid, ethyl maltol, and tartaric acid.

Solid and liquid compositions can also be dyed using any pharmaceutically acceptable colorant to improve their appearance and/or facilitate patient identification of the product and unit dosage level.

In liquid pharmaceutical compositions of the present invention, Danicopan and any other solid excipients are dissolved or suspended in a liquid carrier such as water, vegetable oil, alcohol, polyethylene glycol, propylene glycol, or glycerin.

Liquid pharmaceutical compositions can contain emulsifying agents to disperse uniformly throughout the composition an active ingredient or other excipient that is not soluble in the liquid carrier. Emulsifying agents that can be useful in liquid compositions of the present invention include, for example, gelatin, egg yolk, casein, cholesterol, acacia, tragacanth, chondrus, pectin, methyl cellulose, carbomer, cetostearyl alcohol, and cetyl alcohol.

Liquid pharmaceutical compositions of the present invention can also contain a viscosity enhancing agent to improve the mouth-feel of the product and/or coat the lining of the gastrointestinal tract. Such agents include acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth, and xanthan gum.

Sweetening agents such as sorbitol, saccharin, sodium saccharin, sucrose, aspartame, fructose, mannitol, and invert sugar can be added to improve the taste.

Preservatives and chelating agents such as alcohol, sodium benzoate, butylated hydroxyl toluene, butylated hydroxyanisole, and ethylenediamine tetraacetic acid can be added at levels safe for ingestion to improve storage stability.

According to the present invention, a liquid composition can also contain a buffer such as gluconic acid, lactic acid, citric acid, or acetic acid, sodium gluconate, sodium lactate, sodium citrate, or sodium acetate. Selection of excipients and the amounts used can be readily determined by the formulation scientist based upon experience and consideration of standard procedures and reference works in the field.

The solid compositions of the present invention include powders, granulates, aggregates, and compacted compositions. The dosages include dosages suitable for oral, buccal, rectal, parenteral (including subcutaneous, intramuscular, and intravenous), inhalant, and ophthalmic administration. Although the most suitable administration in any given case will depend on the nature and severity of the condition being treated, the most preferred route of the present invention is oral. The dosages can be conveniently presented in unit dosage form and prepared by any of the methods well-known in the pharmaceutical arts.

Dosage forms include solid dosage forms like tablets, powders, capsules, suppositories, sachets, troches, and lozenges, as well as liquid syrups, suspensions, and elixirs.

The dosage form of the present invention can be a capsule containing the composition, preferably a powdered or granulated solid composition of the invention, within either a hard or soft shell. The shell can be made from gelatin and optionally contain a plasticizer such as glycerin and sorbitol, and an opacifying agent or colorant.

The active ingredient and excipients can be formulated into compositions and dosage forms according to methods known in the art.

A composition for tableting or capsule filling can be prepared by wet granulation. In wet granulation, some or all of the active ingredients and excipients in powder form are blended and then further mixed in the presence of a liquid, typically water, which causes the powders to clump into granules. The granulate is screened and/or milled, dried, and then screened and/or milled to the desired particle size. The granulate can then be tableted, or other excipients can be added prior to tableting, such as a glidant and/or a lubricant.

A tableting composition can be prepared conventionally by dry blending. For example, the blended composition of the actives and excipients can be compacted into a slug or a sheet and then comminuted into compacted granules. The compacted granules can subsequently be compressed into a tablet.

As an alternative to dry granulation, a blended composition can be compressed directly into a compacted dosage form using direct compression techniques. Direct compression produces a more uniform tablet without granules. Excipients that are particularly well suited for direct compression tableting include microcrystalline cellulose, spray dried lactose, dicalcium phosphate dihydrate, and colloidal silica. The proper use of these and other excipients in direct compression tableting is known to those in the art with experience and skill in particular formulation challenges of direct compression tableting.

A capsule filling of the present invention can comprise any of the aforementioned blends and granulates that were described with reference to tableting, but they are not subjected to a final tableting step.

The solid state forms of Danicopan as defined herein as well as the pharmaceutical compositions or formulations comprising them can be used as medicaments, particularly for treating complement mediated diseases, preferably for the treatment of patients with paroxysmal nocturnal hemoglobinuria (PNH), optionally as an add-on therapy to a complement component 5 inhibitor (such as ravulizumab or eculizumab), or for the treatment of geographic atrophy in age-related macular degeneration, comprising administering a therapeutically effective amount of the solid state form of the present disclosure, or at least one of the above pharmaceutical compositions or formulations, to a subject suffering from paroxysmal nocturnal hemoglobinuria (PNH), or otherwise in need of the treatment.

The present disclosure also provides the uses of the solid state form of Danicopan of the present disclosure, or at least one of the above pharmaceutical compositions or formulations, for the manufacture of medicaments for treating complement mediated diseases, preferably for treating paroxysmal nocturnal hemoglobinuria (PNH) optionally as an add-on therapy to a component 5 inhibitor, particularly wherein the component 5 inhibitor is ravulizumab or eculizumab, or for the treatment of geographic atrophy in age-related macular degeneration.

Having described the disclosure with reference to certain preferred embodiments, other embodiments will become apparent to one skilled in the art from consideration of the specification. The disclosure is further illustrated by reference to the following examples describing in detail the preparation of the composition and methods of use of the disclosure. It will be apparent to those skilled in the art that many modifications, both to materials and methods, may be practiced without departing from the scope of the disclosure.

Analytical Methods

Powder X-ray Diffraction was performed on an X-Ray powder diffractometer Bruker D8 Advance; CuK radiation ($\lambda$=1.5418 Å); Lynx eye detector; laboratory temperature 22-25° C.; PMMA specimen holder ring. Prior to analysis, the samples were gently ground by means of mortar and pestle in order to obtain a fine powder. The ground sample was adjusted into a cavity of the sample holder and the surface of the sample was smoothed by means of a cover glass.

Measurement parameters: Scan range: 2-40 degrees 2-theta; Scan mode: continuous; Step size: 0.05 degrees;

Time per step: 0.5 s; Sample spin: 30 rpm; Sample holder: PMMA specimen holder ring with silicon low background.

All X-Ray Powder Diffraction peak values are calibrated with regard to standard silicon spiking in the sample.

EXAMPLES

Danicopan can be obtained by any procedure described in the literature, for example using the syntheses procedure reported in U.S. Pat. No. 10,253,053.

Example 1: Preparation of Danicopan Form DT1

Danicopan (0.04 g) was dissolved in 2 mL of vinyl acetate at 60° C. A precooled (at 0° C.) Methyl tert-butyl ether was added to the solution at 60° C. The hot solution was cooled to 0° C. in 1 hour, maintained at 0° C. for 20 hours under stirring to isolate the obtained solid by filtration at RT and drying under vacuum at 25° C. for 1 hour. The obtained Danicopan was designated Form DT1 by XRD (FIG. 1).

Example 2: Preparation of Danicopan Form DT1

Danicopan (3.0 g) was dissolved in 125 mL of vinyl acetate at 60° C. The clear solution was filtered at 60° C., maintained at 60° C. for 15 minutes and cooled to 25° C. in 1 hour. The obtained solid was isolated by filtration at RT, dried under vacuum at 25° C. for 1 hour and analyzed by XRD to obtain Danicopan designated as Form DTI (FIG. 1).

Example 3. Preparation of Danicopan Form DT2

Danicopan form DT1 (1.0 g) was suspended in 120 mL of n-heptane by heating to 60° C. for 3 days under stirring. The hot suspension was cooled to 25° C. in 1 hour, and the solid was isolated by filtration at RT, dried under vacuum at 60° C. for 6 hours and analyzed by XRD to obtain Danicopan designated as Form DT2 (FIG. 2).

Example 4. Preparation of Danicopan Form DT2

Danicopan Form DT1 (0.2 g) was suspended in Cyclohexane (15 ml) at 60° C. for 2 days, under stirring. The hot suspension was cooled to 25° C. in 1 hour and the obtained solid was isolated by filtration at RT, dried under vacuum at 60° C. for 6 hours and analyzed by XRD to confirm Danicopan Form DT2 (FIG. 2).

Example 5. Preparation of Danicopan Pure Form DT2

Amorphous Danicopan (5.0 g, prepared according to examples 6 or 7) was suspended in 120 mL of n-heptane at 70° C. for 1 day under stirring. The hot solution was cooled to 25° C. in 1 hour and the obtained solid was isolated by filtration at RT, dried under vacuum at 60° C. for 24 hours and analyzed by XRD to obtain Danicopan designated purified Form DT2 as shown in FIG. 3.

Example 6. Preparation of Amorphous Danicopan

Danicopan (5.0 g) was dissolved in 50 mL of Dichloromethane at 35-40° C. and clear solution was filtered through 0.45 micron filter. The solution was subjected to distillation under reduced pressure at 40-45° C. for 30-45 minutes, and the obtained solid was dried under vacuum at 60° C. for 1 hour to produce Amorphous Danicopan defined by XRPD in FIG. 4.

Example 7. Preparation of Amorphous Danicopan

Danicopan (2.0 g) was dissolved in 5 mL of THF at 50° C. and was filtered through 0.45 micron filter. A precooled (0° C.) n-heptane (15 mL) was added to the filtered solution to observe immediate precipitation stirred at 0° C. for 1 hour at 0° C. The obtained solid was isolated by filtration under suction at 25° C., dried under vacuum at 60° C. for 1 hour and analyzed by XRD to obtain Amorphous Danicopan.

Example 8. Preparation of Crystalline Danicopan Form DT3

Danicopan (0.02 g) was dissolved in 0.1 mL of Dimethylacetamide at 25° C. The clear solution was covered with aluminum foil with pinholes and kept at 25° C. for 15 days. The obtained solid was isolated by filtration at RT, dried under vacuum at 25° C. for 1 hour and analyzed by XPD to obtain Danicopan designated Form DT3 described in FIG. 5.

Example 9. Preparation of Crystalline Danicopan Form DT4

Danicopan (0.5 g) was dissolved in 5 mL of Dimethylformamide at 70° C. The Clear solution was filtered and kept at 0-5° C. for 3 days. The Solid obtained was filtered at RT and dried under vacuum at 60° C. for 4 hours. The obtained solid analyzed by XRD and designated as Danicopan Form DT4 (FIG. 6).

Example 10. Preparation of Crystalline Danicopan Form DT5

Danicopan (0.05 g) was added to 1 mL of Propionic acid: water mixture (50:50 V/V) and the obtained slurry was kept at 25° C. for 3 days under stirring. The solid was isolated by filtration, dried under vacuum at 60° C. for 1 hour and analyzed by XRPD to obtain Danicopan designated Form DT5 (FIG. 7).

Example 11. Preparation of Crystalline Danicopan Form DT6

Danicopan (0.05 g) was dissolved in 0.1 mL of acetophenone at 50° C. The hot solution was immediately transferred to dry ice in acetone bath at (−70° C.) for 10 minutes. The obtained solid was isolated by filtration at RT, dried under vacuum at 60° C. for 1 hour and analyzed by XRPD to produce Danicopan designated Form DT6 (FIG. 8).

Example 12. Preparation of Crystalline Danicopan Form DT2

Danicopan amorphous form (0.5 g) was dissolved in 2.5 mL of Diethyl carbonate or in diethyl ketone at 60° C. The clear solution was cooled to 25° C. in 1 hour and the obtained solid was filtered at RT, dried under vacuum at 60° C. for 6 hours and analyzed by XRD to obtain Danicopan Form DT2.

Example 13: Preparation of Danicopan Form DT1

Danicopan (0.04 g) was dissolved in 2 mL of vinyl acetate at 60° C. A precooled (at 0° C.) Methyl tert-butyl ether (6 ml) was added to the solution at 60° C. The hot solution was cooled to 0° C. in 1 hour, maintained at 0° C. for 20 hours under stirring to isolate the obtained solid by filtration at RT and drying under vacuum at 25° C. for 1 hour. The obtained Danicopan was designated Form DT1 by XRD (FIG. 1).

Example 14: Stability Experiments

Storage Stability at Different Relative Humidities

Samples of Danicopan Form DT2 were subjected to conditions of different relative humidities at ambient temperature. XRPD analysis was performed on the samples after 7 days. The results are shown in Table 1 below:

TABLE 1

| | Danicopan Form DT2 Relative humidity | | | | |
|---|---|---|---|---|---|
| | 20% | 40% | 60% | 80% | 100% |
| XRPD analysis results | No change | No change | No change | No change | No change |

These results demonstrate that Danicopan Form DT2 is stable after exposure to high and low relative humidity for at least 7 days.

Samples of Danicopan Form DT2 were packaged in polyethylene/aluminum bags and subjected to different relative humidities conditions at different temperatures. XRPD analysis was performed on the samples after 6 months stability. The results are shown in Table 2 below:

TABLE 2

| | Danicopan Form DT2 Conditions (6 months) | |
|---|---|---|
| | 25° C., 60% RH | 40° C., 75% RH |
| XRPD analysis results | No change | No change |

The results demonstrate that Danicopan Form DT2 is stable after exposure to high and low relative humidity at different temperatures for at least 6 months, indicating that this crystalline form has good storage stability.

Grinding Experiments

Samples of Danicopan Form DT2 were subjected to strong grinding, and to solvent drop grinding in water and ethanol. Grinding was carried out on the samples alone, or in the presence of ethanol or water. In these experiments, about 20 mg of the sample is placed in a mortar and ground with a pestle for 2 minutes. The solvent, when used, as added to the crystalline material before grinding, in a volume of 10 microlitres. XRPD analysis performed on each of the samples after the grinding experiment, confirmed no change in the starting material (Table 3):

TABLE 3

| Danicopan Form DT2 | |
|---|---|
| Condition | XRPD analysis results |
| Strong grinding | No change |
| Solvent-drop grinding (ethanol) | No change |
| Solvent-drop grinding (water) | No change |

The results demonstrate that Danicopan Form DT2 is resistant to polymorphic changes and is highly suitable for preparing pharmaceutical formulations.

Thermal Stability

A sample of Danicopan Form DT2 was subjected to heating up to 100° C. for 30 minutes. XRPD analysis of the sample confirmed no change in the starting material (Table 4):

TABLE 4

| Danicopan Form DT2 | |
|---|---|
| Condition | Result |
| Heating 100° C., 30 minutes | Stable |

Stability to Compression

Samples of Danicopan Form DT2 were subjected to pressures of 19841 $kg/m^2$ and 39682 $kg/m^2$. XRPD analysis was performed on the samples after 1-5 minutes. The results are shown in Table 5 below:

TABLE 5

| | XRPD analysis results Pressure ($kg/m^2$) | |
|---|---|---|
| | 19841 | 39682 |
| Danicopan Form DT2 | No change | No change |

Accordingly, Danicopan Form DT2 is stable under high pressure conditions, making it highly suitable for pharmaceutical processing.

The invention claimed is:

1. A crystalline form of Danicopan, designated form DT2, which is characterized by an XRPD pattern having peaks at 8.5, 12.9, 14.7, 17.0 and 19.6 degrees 2-theta±0.2 degrees 2-theta.

2. A crystalline form of Danicopan according to claim 1, which is characterized by an XRPD pattern having peaks at 8.5, 12.9, 14.7, 17.0 and 19.6 degrees 2-theta±0.2 degrees 2-theta, and also having one, two, three or four additional peaks selected from 11.5, 22.0, 22.5 and 30.9 degrees two theta±0.2 degrees two theta; or combinations of these data.

3. A crystalline form of Danicopan according to claim 1, which is characterized by an XRPD pattern having peaks at 8.5, 12.9, 14.7, 17.0 and 19.6 degrees two theta±0.2 degrees two theta, and also having one, two, three, four, or optionally five additional peaks selected from 20.9, 22.0, 22.5, 27.0 and 30.9 degrees two theta±0.2 degrees two theta.

4. A crystalline form of Danicopan according to claim 1, which is characterized by an X-ray powder diffraction pattern having peaks at 8.5, 11.5, 12.9, 14.7, 17.0, 19.6, 22.0, 22.5 and 30.9 degrees two theta±0.2 degrees two theta.

5. A crystalline form of Danicopan according to claim 1, which is characterized by an X-ray powder diffraction pattern having peaks at 8.5, 12.9, 14.7, 17.0, 19.6, 20.9, 22.0, 22.5, 27.0 and 30.9 degrees two theta±0.2 degrees two theta.

6. A crystalline form of Danicopan according to claim 1, which is characterized by an X-ray powder diffraction pattern substantially as depicted in FIG. 2 or FIG. 3.

7. A crystalline form of Danicopan according to claim 1, which contains no more than about 20% any other crystalline forms of Danicopan.

8. A crystalline form of Danicopan according to claim 1, which contains no more than about 20% of amorphous Danicopan.

9. A crystalline form of Danicopan according to claim 1, which is chemically pure.

10. A pharmaceutical composition comprising a crystalline form of Danicopan according to claim 1 and at least one pharmaceutically acceptable excipient.

11. A process for preparing a pharmaceutical composition comprising combining a crystalline form of Danicopan according to claim 1 with at least one pharmaceutically acceptable excipient.

12. A medicament comprising the crystalline form of Danicopan according to claim 1.

13. A method of treating paroxysmal nocturnal hemoglobinuria (PNH), other complement mediated diseases, or geographic atrophy in age-related macular degeneration, comprising administering a crystalline form of Danicopan according claim 1 to a patient in need of treatment.

14. The method of claim 13, wherein the crystalline form of Danicopan is administered to the patient as an add-on therapy in combination with a component 5 inhibitor.

15. The method of claim 14, wherein the component 5 inhibitor is ravulizumab or eculizumab.

* * * * *